(12) United States Patent
Yoshida et al.

(10) Patent No.: US 7,674,771 B2
(45) Date of Patent: Mar. 9, 2010

(54) ANTIMICROBIAL PEPTIDES AND UTILIZATION OF THE SAME

(75) Inventors: Tetsuhiko Yoshida, Aichi (JP); Yoshinao Yamada, Aichi (JP); Masayoshi Kume, Aichi (JP); Hiroki Kourai, Tokushima (JP)

(73) Assignee: Toagosei Co., Ltd, Tokyo (JP)

( * ) Notice: Subject to any disclaimer, the term of this patent is extended or adjusted under 35 U.S.C. 154(b) by 526 days.

(21) Appl. No.: 10/577,688

(22) PCT Filed: Oct. 25, 2004

(86) PCT No.: PCT/JP2004/015803

§ 371 (c)(1),
(2), (4) Date: Apr. 28, 2006

(87) PCT Pub. No.: WO2005/049819

PCT Pub. Date: Jun. 2, 2005

(65) Prior Publication Data

US 2007/0032431 A1 Feb. 8, 2007

(30) Foreign Application Priority Data

Oct. 29, 2003 (JP) .............................. 2003-369595

(51) Int. Cl.
*A61K 38/03* (2006.01)
(52) U.S. Cl. .............................. 514/13; 514/14; 514/15; 514/16; 530/326; 530/327; 530/328; 530/329
(58) Field of Classification Search ....................... None
See application file for complete search history.

(56) References Cited

U.S. PATENT DOCUMENTS

| | | | |
|---|---|---|---|
| 5,547,939 | A | 8/1996 | Selsted |
| 5,789,542 | A | 8/1998 | McLaughlin et al. |
| 5,807,746 | A | 9/1998 | Lin et al. |
| 5,877,282 | A | 3/1999 | Nadler et al. |
| 5,962,415 | A | 10/1999 | Nadler |
| 6,043,339 | A | 3/2000 | Lin et al. |
| 6,180,604 | B1 | 1/2001 | Fraser et al. |
| 6,191,254 | B1 | 2/2001 | Falla et al. |
| 6,303,575 | B1 | 10/2001 | Selsted |
| 6,388,056 | B1* | 5/2002 | Sundstrom et al. ........... 530/371 |
| 6,426,191 | B1* | 7/2002 | Ford et al. .................... 435/7.8 |
| 6,476,189 | B1 | 11/2002 | Yamakawa et al. |
| 2002/0137685 | A1 | 9/2002 | Catania et al. |
| 2003/0129156 | A1 | 7/2003 | Lipton et al. |

FOREIGN PATENT DOCUMENTS

| | | |
|---|---|---|
| JP | 11-71399 A | 3/1999 |
| JP | 2000-63400 | 2/2000 |
| JP | 2001-186887 | 7/2001 |
| WO | 9402610 | 2/1994 |
| WO | 9636692 | 11/1996 |
| WO | 9851794 | 11/1998 |
| WO | 9926971 | 6/1999 |
| WO | 9929721 | 6/1999 |
| WO | 9967284 | 12/1999 |
| WO | 0009553 | 2/2000 |
| WO | 0059527 | 10/2000 |
| WO | 0109175 | 2/2001 |
| WO | 0208266 | 1/2002 |
| WO | 0210201 | 2/2002 |
| WO | 0236612 | 5/2002 |
| WO | 02078524 | 10/2002 |
| WO | 02094868 | 11/2002 |
| WO | WO03/000277 | * 1/2003 |

OTHER PUBLICATIONS

International Search Report for PCT/JP2004/015803, Apr. 12, 2005.
International Preliminary Examination Report for PCT/JP2004/015803, Sep. 16, 2005.
Written Opinion for PCT/JP2004/015803, Feb. 9, 2005.
Supplementary European Search Report for PCT/JP2004/015803, Jun. 13, 2007.
Ghosh, A., et al., Isolation of a laminin-binding protein from the protozoan parasite *Leishmania donovani* that may mediate cell adhesion, Biochem J, (1999) vol. 337, No. 3, p. 551-8.
Ardini, E., et al., The 67-kDa laminin receptor originated from a ribosomal protein that acquired a dual function during evolution, Mol Biol Evol, (1998) vol. 15, No. 8, p. 1017-25.
Bandyopadhyay, K., et al., Role of 67 kDa cell surface laminin binding protein of *Leishmania donovani* in pathogenesis, J Biochem (Tokyo), (2001)vol. 130, No. 1, p. 141-8.
Valkonen, K. H., et al., Binding of basement-membrane laminin by *Escherichia coli*, Mol Microbiol, (1991) vol. 5, No. 9, p. 2133-41.
Castronovo, V., et al., Functional domains of the 67-kDa laminin receptor precursor, J Biol Chem, (1991) vol. 266, No. 30, p. 20440-6.
Nahoko Kobayashi et al., "Molecular Design of Peptide-based Antimicrobial Agent," The Society for Antibacterial and Antifungal Agents, Japan, Abstracts of the Meeting, (May 25, 2003), vol. 30, p. 137, IIDp-5 w/English translation.
Pei, L., et al., Functional studies of a fibrinogen binding protein from *Staphylococcus epidermidis*, Infect Immun, (1999) vol. 67, No. 9, p. 4525-30.
Mariagrazia Cutuli et al., Antimicrobial effects of a-MSH peptides, Journal of Leukocyte Biology, vol. 67, Feb. 2000, pp. 233-239.
Richards DB et al., "Effect of alpha-MSH 11-13 (lysine-proline-valine) on fever in the rabbit," Peptides, Jul.-Aug. 1984; 5(4): 815-7, Abstract, PubMed.
Laure Beven et al., "Effects on mollicutes (wall-less bacteria) of synthetic peptides comprising a signal peptide or a membrane fusion peptide, and a nuclear localization sequence (NLS)—a comparison with melittin," Biochim Biophys Acta Oct. 23, 1997:1329(2), pp. 357-369.

(Continued)

Primary Examiner—Anish Gupta
(74) Attorney, Agent, or Firm—Turocy & Watson, LLP

(57) ABSTRACT

Antimicrobial peptide provided by present invention is an artificially designed antimicrobial peptide that does not occur naturally, and includes a sequence composed of at least 6 contiguous amino acid residues selected from an amino acid sequence constituting laminin binding site (LBS), or said sequence with one or a plurality of amino acid residue(s) conservatively replaced, and an amino acid sequence that can express antimicrobial activity against at least one kind of bacteria or fungi. It is desirable that the total number of amino acid residues is 100 or less.

4 Claims, No Drawings

OTHER PUBLICATIONS

Laurent Chaloin et al., "Ionic channels formed by a primary amphipathic peptide containing a signal peptide and a nuclear localization sequence," Biochim biophys Acta Oct. 15, 1998: 1375(1-2), pp. 52-60.

Shai, Yechiel, "From Innate Immunity to de-Novo Designed Antimicrobial Peptides," Current Pharmaceutical Design, 2002, vol. 8, pp. 715-725.

* cited by examiner

ANTIMICROBIAL PEPTIDES AND UTILIZATION OF THE SAME

TECHNICAL FIELD

The present invention relates to oligopeptide or polypeptide having antimicrobial property (hereinafter, antimicrobial peptide) and comprising independent peptide chains in the form that does not occur naturally, and their utilization. More specifically, the present invention relates to antimicrobial agent (composition) having such antimicrobial peptide as the main component.

BACKGROUND ART

It is generally believed that antimicrobial peptide has a broad antimicrobial spectrum such that drug resistant bacterium hardly appears, and therefore antimicrobial peptide is expected to be used for the purpose of preventing and treating bacterial infectious diseases in human beings and animals or providing antimicrobial properties to products such as food. A large number of antimicrobial peptides have been isolated from various animals and plants to date.

As examples, antimicrobial peptides disclosed in International Publication No. WO98/51794, International Publication No. WO99/26971, International Publication No. WO00/09553, International Publication No. WO00/59527, International Publication No. WO01/09175, Japanese Laid-Open Patent Publication No. 2000-63400, Japanese Laid-Open Patent Publication No. 2001-186887, and 'The 67-kDa Laminin Receptor Originated from a Ribosomal Protein that Acquired a Dual Function During Evolution', Elena Ardini et al., Volume 15, Issue No. 8, 1998, p. 1017-1025, are being identified.

Every antimicrobial peptide disclosed in each aforementioned publication is discovered in and isolated from peptide that originally exists as antimicrobial peptide in nature (or peptide of which a part of the amino acid sequence of an isolated natural antimicrobial peptide is being modified). As long as these peptides that originally exist as antimicrobial peptides are being used as the main component, it is difficult to develop antimicrobial agent having antimicrobial performance that exceeds the antimicrobial activity and the antimicrobial spectrum accomplished by such original peptides in nature.

One of the objects of the present invention is to provide, without utilizing the developmental approach of antimicrobial agent including the conventional antimicrobial peptides, antimicrobial peptides composed of artificially designed amino acid sequences that are different from peptides existing and functioning as antimicrobial peptides in nature, and polynucleotides encoding such peptides. In addition, one of the objects is to provide antimicrobial agents (pharmaceutical compositions) having such antimicrobial peptides as the main component.

DISCLOSURE OF INVENTION

The antimicrobial peptides provided by the present invention are peptides developed from an approach different from the conventionally known antimicrobial peptides. Particularly, antimicrobial peptides created by utilizing amino acid sequence included in a polypeptide that is different from the polypeptide serving as antimicrobial peptide in nature.

An artificially synthesized antimicrobial peptide described in the present specification that does not occur naturally is a peptide including a sequence composed of at least 6 contiguous amino acid residues selected from an amino acid sequence constituting laminin binding site (LBS), or said sequence with one or a plurality of amino acid residue(s) conservatively replaced, and an amino acid sequence that can express antimicrobial activity against at least one kind of bacteria or fungi. It is desirable that the total number of amino acid residues is 100 or less.

In addition, another artificially synthesized antimicrobial peptide described in the present specification that does not occur naturally is a peptide including a sequence composed of at least 6 contiguous amino acid residues selected from an amino acid sequence constituting laminin binding site (LBS), or said sequence with one or a plurality of amino acid residue(s) conservatively replaced, and a partial sequence linked in tandem to the C-terminal and/or N-terminal of said sequence, where the partial sequence is a high basic partial sequence and more than half of amino acid residues constituting the partial sequence composed of 3 or more contiguous amino acid residues are lysine or arginine. It is desirable that the total number of amino acid residues is 100 or less.

Here, "artificially synthesized antimicrobial peptide that does not occur naturally" refers to antimicrobial peptide whose peptide chain alone does not independently occur in nature, but peptide segment that is artificially produced by chemical synthesis or biosynthesis (i.e., produced based on genetic engineering). Here, "antimicrobial peptide" is a term referring to amino acid polymer having a plurality of peptide bonds displaying antimicrobial activity against at least one kind of microbe, and is not limited by the number of the amino acid residues constituting the peptide chain. The antimicrobial peptide in this specification also includes oligopeptides having 10 and below amino acid residues or polypeptides containing 10 or more amino acid residues. Here, unless otherwise specified, "amino acid residue" is a term including N-terminal amino acid and C-terminal amino acid of the peptide chain.

The inventors of the present invention discovered that peptide chain designed by combining a part of the amino acid sequence from a part known as laminin binding site (LBS) found in proteins that functions as receptors for laminin, which is non-collagen glycoprotein, and the above defined sequence, more specifically the amino acid sequence that can express antimicrobial activity against at least one kind of bacteria or fungi and/or the high basic partial sequence (hereinafter collectively refers to as "antimicrobial associated sequence"), can exhibits high antimicrobial activity against various microbes, thereby leading to the accomplishment of the present invention. Here, unless otherwise specified, "laminin binding site" is a term encompassing the general amino acid sequence known as amino acid sequence constituting the laminin binding site of laminin receptor, and is not limited to specific organism origin or specific amino acid sequence.

Since the antimicrobial peptide of the present invention includes, as main components, a sequence composed of at least 6 contiguous amino acid residues selected from an amino acid sequence constituting laminin binding site (LBS) (specifically, amino acid sequence known for constituting LBS) or said sequence with one or a plurality of amino acid residue(s) conservatively replaced (hereinafter abbreviated as "LBS sequence"), the antimicrobial peptide can exhibit high antimicrobial activity against at least one kind of bacteria (gram-negative bacteria and/or gram-positive bacteria) or fungi.

Desirable antimicrobial peptide is characterized in that the sequence composed of at least 6 contiguous amino acid residues is an amino acid sequence shown in any one of SEQ ID NOs: 1-9, or a sequence including said amino acid sequence. These sequences shown in the Sequence Nos. are palindrome sequences (for example SEQ ID NO: 1) known for deeply involved in binding with laminin or the same kind of sequences having the same kind of laminin binding function (see the aforementioned non-patent document 1). By having LBS sequence including these sequences (can be said sequences with one or a plurality of amino acid residue(s) conservatively replaced) and the above-described antimicrobial associated sequence, extremely high antimicrobial activity against at least one kind of bacteria (gram-negative bacteria and/or gram-positive bacteria) or fungi can be exhibited.

As for the structure of the antimicrobial peptide, it is particularly desirable that the peptide includes an amino acid sequence shown in any one of SEQ ID NOs: 10-30 or said sequence with one or a plurality of amino acid residue(s) conservatively replaced, or the peptide is composed of said sequence.

Furthermore, it is desirable that the antimicrobial peptide is a peptide with at least one amino acid residue being amidated. The structural stability (for example, protease resistance) of the antimicrobial peptide can be improved by amidating the carboxyl group of the amino acid residue (typically the C-terminal amino acid residue of the peptide chain).

Furthermore, it is desirable that the antimicrobial peptide is a peptide of which the total number of amino acid residues constituting a peptide chain is 20 or less. Chemical synthesis for peptide with such short peptide chain is easy, and antimicrobial peptide can be easily provided.

Furthermore, the present invention provides a method for producing the antimicrobial peptide described in the present specification. More specifically, one of the method for producing the antimicrobial peptide provided by the present invention includes determining a sequence composed of at least 6 contiguous amino acid residues selected from an amino acid sequence (therefore, sequence known as LBS) constituting LBS, or said sequence with one or a plurality of amino acid residue(s) conservatively replaced, designing a peptide chain including said determined sequence and an amino acid sequence that can express antimicrobial activity against at least one kind of bacteria or fungi, and synthesizing said designed peptide chain.

Furthermore, another method for producing the antimicrobial peptide includes determining a sequence composed of at least 6 contiguous amino acid residues selected from an amino acid sequence (therefore, sequence known as LBS) constituting LBS, or said sequence with one or a plurality of amino acid residue(s) conservatively replaced, designing a peptide chain including said determined sequence and a partial sequence linked in tandem to the N-terminal and/or C-terminal of said determined sequence, where the partial sequence is a high basic partial sequence and more than half of amino acid residues constituting the partial sequence composed of 3 or more contiguous amino acid residues are lysine or arginine, and synthesizing said designed peptide chain.

With regard to the design of the peptide chain, it is desirable to design a peptide of which the total number of amino acid residues is 100 or less. Peptide with short peptide chain can be easily produced and purified by, for example, a general chemical synthesis method.

Furthermore, the present invention provides an antimicrobial agent (typically a composition that can be used in the medical field and the hygieiological field) including at least one of the antimicrobial peptides described in the present specification and a pharmaceutically acceptable carrier. An antimicrobial agent including, as a main component, an antimicrobial peptide of which the total number of amino acid residues is 100 or less is desirable (more preferably 20 or less). Antimicrobial agent including peptide with such short peptide chain (therefore antimicrobial peptide with relatively low molecular mass) is easy to utilize, and can be a preferred antimicrobial agent for in vivo or/and ex vivo usage.

Furthermore, the present invention provides an artificially designed polynucleotide that does not occur naturally and includes or substantially composed of a nucleotide sequence, which encodes any of the antimicrobial peptide described in the present specification, and/or a nucleotide sequence complementary to said sequence. In this specification, "polynucleotide" is a general term referring to polymer (nucleic acid) in which a plurality of nucleotides are bound by phosphodiester bonds, and is not limited by the number of the nucleotides. The polynucleotide in the present specification may include DNA fragments and RNA fragments having various lengths. In addition, "artificially designed polynucleotide that does not occur naturally" refers to polynucleotide whose nucleotide chain (total length) alone does not independently occur in nature, but is artificially chemically synthesized or biosynthesized (i.e., produced based on genetic engineering).

A polynucleotide including or substantially composed of a nucleotide sequence, which encodes any of the amino acid sequence shown in SEQ ID NOs: 10-30 (or said sequence with one or a plurality of amino acid residue(s) conservatively replaced), and/or a nucleotide sequence complementary to said sequence is desirable.

The antimicrobial peptide having the primary structure including LBS sequence and the antimicrobial associated sequence provided by the present invention can exhibit high antimicrobial activity against various kinds of gram-positive bacteria, gram-negative bacteria and/or fungi. Therefore, the antimicrobial peptide of the present invention can be utilized as the main constituent of antimicrobial agent. Moreover, antimicrobial agent including such antimicrobial peptide can be utilized for in vivo or ex vivo usage.

<Sequence Listing Free Text>

| | |
|---|---|
| SEQ ID NO: 10 | designed antimicrobial peptide containing an amide group in its terminal |
| SEQ ID NO: 11 | designed antimicrobial peptide containing an amide group in its terminal |
| SEQ ID NO: 12 | designed antimicrobial peptide containing an amide group in its terminal |
| SEQ ID NO: 13 | designed antimicrobial peptide containing an amide group in its terminal |
| SEQ ID NO: 14 | designed antimicrobial peptide containing an amide group in its terminal |
| SEQ ID NO: 15 | designed antimicrobial peptide containing an amide group in its terminal |
| SEQ ID NO: 16 | designed antimicrobial peptide containing an amide group in its terminal |
| SEQ ID NO: 17 | designed antimicrobial peptide containing an amide group in its terminal |
| SEQ ID NO: 18 | designed antimicrobial peptide containing an amide group in its terminal |
| SEQ ID NO: 19 | designed antimicrobial peptide containing an amide group in its terminal |

-continued

<Sequence Listing Free Text>

| | |
|---|---|
| SEQ ID NO: 20 | designed antimicrobial peptide containing an amide group in its terminal |
| SEQ ID NO: 21 | designed antimicrobial peptide containing an amide group in its terminal |
| SEQ ID NO: 22 | designed antimicrobial peptide containing an amide group in its terminal |
| SEQ ID NO: 23 | designed antimicrobial peptide containing an amide group in its terminal |
| SEQ ID NO: 24 | designed antimicrobial peptide containing an amide group in its terminal |
| SEQ ID NO: 25 | designed antimicrobial peptide |
| SEQ ID NO: 26 | designed antimicrobial peptide containing an amide group in its terminal |
| SEQ ID NO: 27 | designed antimicrobial peptide containing an amide group in its terminal |
| SEQ ID NO: 28 | designed antimicrobial peptide containing an amide group in its terminal |
| SEQ ID NO: 29 | designed antimicrobial peptide containing an amide group in its terminal |
| SEQ ID NO: 30 | designed antimicrobial peptide containing an amide group in its terminal |
| SEQ ID NO: 31 | designed peptide containing an amide group in its terminal |
| SEQ ID NO: 32 | designed peptide containing an amide group in its terminal |
| SEQ ID NO: 33 | designed peptide containing an amide group in its terminal |
| SEQ ID NO: 34 | designed peptide containing an amide group in its terminal |
| SEQ ID NO: 35 | designed peptide containing an amide group in its terminal |
| SEQ ID NO: 36 | designed peptide containing an amide group in its terminal |
| SEQ ID NO: 37 | designed peptide containing an amide group in its terminal |
| SEQ ID NO: 38 | designed antimicrobial peptide containing an amide group in its terminal |

BEST MODE FOR CARRYING OUT THE INVENTION

Hereinafter, preferred embodiments of the present invention will be described. The matters that are other than those specifically mentioned in this specification (e.g., primary structure or chain length of antimicrobial peptide) and that are necessary for performing the present invention (for example, general matters related to peptide synthesis, polynucleotide synthesis, and preparation of antimicrobial agent (pharmaceutical composition) including peptide as a component) can be considered as matters of design by those skilled in the art based on the conventional technology in the fields of organic chemistry, biochemistry, genetic engineering, protein engineering, molecular biology, pharmaceuticals, medicine, hygieiology and the like. The present invention can be performed based on the contents described in this specification and the common technical knowledge in the field. In the following description, according to circumstances, amino acids are also expressed in the single character code based on the IUPAC-IUB nomenclature for amino acids.

Antimicrobial peptides described in the present specification are peptides that are artificially synthesized and do not occur naturally, and are short polypeptides and oligopeptides having LBS sequence and antimicrobial associated sequence. Particularly, antimicrobial peptides of the present invention are peptide segments in which LBS sequence and antimicrobial associated sequence are in proximity with each other, and therefore is a substance that distinctively differs from various polypeptides (peptide chains) existing in nature.

It is desirable that the percentage of LBS sequence and antimicrobial associated sequence with respect to the entire amino acid sequence is 40% or more, or the percentage is more desirable to be 70% or more of the total amino acids constituting the peptide chain, or even more desirable to be 90% or more.

It is desirable that all the amino acid residues constituting the antimicrobial peptides in the present invention to be L-amino acids, but the amino acid residues can also be partially or entirely substituted with D-amino acids as long as antimicrobial activity is not lost.

The chain length (number of amino acid residues) of the antimicrobial peptide in the present invention can vary according to the length of the LBS sequence and/or antimicrobial associated sequence included; and although there is no specific limitation, it is desirable that the total number of amino acid residues to be 100 or less, for example an antimicrobial peptide composed of approximately 10 to 100 amino acid resides, more desirably an antimicrobial peptide composed of approximately 10 to 50 amino acid residues, or particularly desirably an antimicrobial peptide composed of approximately 12 to 20 amino acid residues.

Further, although there is no particular limitation regarding the conformation (three-dimensional structure) of the peptide as long as the peptide is antimicrobial under the environment in which it is being used, linear or helical peptide is desirable in view of their difficulty in becoming an immunogen (antigen). Peptide having such a shape hardly constitutes epitope. In view of this, it is desirable for antimicrobial peptide applying to an antimicrobial agent to be linear and having a relatively low molecular weight (typically, the number of amino acid residues: 10 to 30; for example, the number of amino acid residues: 10 to 20).

Conventionally, any sequence composed of at least 6 contiguous amino acid residues selected from (native type) amino acid sequence, which is known as sequence constituting the laminin binding site and found in every kind or organism, can be utilized without modification as the LBS sequence for constituting the antimicrobial peptide. Specific examples include the following 9 kind of sequences: LMWWML (SEQ ID NO:1); LMWWLL (SEQ ID NO:2); CLFWLL (SEQ ID NO:3); LIWYLL (SEQ ID NO:4); VVYWLL (SEQ ID NO:5); LYLGAV (SEQ ID NO:6); LITSKM (SEQ ID NO:7); FFYMVI (SEQ ID NO:8); LLTAKM (SEQ ID NO:9), composed of 6 contiguous amino acid resides selected from sequence, which is known as amino acid sequence constituting the LBS introduced in the aforementioned non-patent document 1. Peptide including one or more kind(s) of the aforementioned as LBS sequence (or a part of an LBS sequence) is desirable. For example, as specific preferable examples, peptide in which any of SEQ ID NOs:1-9 is utilized without modification as LBS sequence, as shown in SEQ ID NOs: 10-30 described hereinafter (see table 1), is desirable.

As long as antimicrobial activity is not lost, not only sequence of native type can be utilized as LBS sequence, but various kinds of LBS sequence that is partially modified can also be utilized. For example, sequence in which several (for example 1 to 3) amino acid residues are conservatively replaced, sequence in which 1, 2 or 3 amino acids are added to the N-terminal and/or C-terminal of a sequence composed of at least 6 contiguous amino acid residues selected from amino acid sequence constituting native type LBS, sequence in which the carboxyl group of the C-terminal amino acid (therefore corresponding to the C-terminal amino acid of the peptide chain) is amidated, and the like are specific examples of such kinds of modified sequence.

Antimicrobial associated sequence for constituting the antimicrobial peptide of the present invention is not limited to specific amino acid sequence, as long as the amino acid sequence is an amino acid sequence that can express antimicrobial activity against at least one kind of bacteria or fungi, or an amino acid sequence (high basic partial sequence) composed of 3 or more contiguous amino acid residues and more than half of the amino acid residues constituting such sequence are basic amino acid (therefore lysine or arginine).

The entire or part of an amino acid sequence in a conventional antimicrobial peptide of which primary structure is known can be utilized as the amino acid sequence that can express antimicrobial activity against at least one kind of bacteria or fungi. It is desirable to utilize antimicrobial peptide composed of relatively short peptide chain generally known as defensins. For example, it is desirable to utilize the entire or part of the amino acid sequence in antimicrobial peptide derive from various insects, such as sarcotoxin, or in polypeptide having antimicrobial activity derive from mammals, such as alpha-melanocyte-stimulating hormone (α-MSH), protegrin-1 (see the example described hereinafter).

The high basic partial sequence is not limited to specific amino acid sequence, as long as it is composed in such a way that more than half of the partial sequence (with 3 or more amino acid residues) linked in tandem to the N-terminal and/or C-terminal of the LBS sequence is basic amino acid residues (therefore lysine or arginine). High basic partial sequence composed of 4 or more amino acid residues (more desirably 5 or more amino acid residues) linked in tandem to the N-terminal and/or C-terminal of the LBS sequence, and where ¾ (75%) or more of such amino acid residues are each either lysine or arginine, is desirable. High basic partial sequence composed of 5 or more amino acid residues, and where ⅘ (80%) or more of such amino acid residues (more desirably all such amino acid residues) are each either lysine or arginine, is particularly desirable.

The antimicrobial peptide of the present invention can include partial sequence that is not present in LBS sequence or antimicrobial associated sequence as long as the antimicrobial property is not lost. Although there is no specific limitation, sequence that can maintain the three-dimensional shape of LBS sequence and antimicrobial associated sequence in a peptide chain is desirable for such partial sequence.

Desirable antimicrobial peptide described herein includes peptide in which the total number of amino acid residues is 100 or less, and in which amino acid residues constituting one, two or more of LBS sequences, and one, two or more of antimicrobial associated sequences are 80% or more, or more desirably 90% or more, of the total amino acid residues constituting the peptide chain. Alternatively, antimicrobial peptide composed of such sequences and part of the linkers (desirably, composed of one to several amino acid residues) interposed between such sequences is also preferred.

Although the antimicrobial peptides represented in SEQ ID NOs: 10-30 are specific preferable examples of the antimicrobial peptide describe herein, this does not imply that preferable peptides are limited to peptides with such amino acid sequences. For example, sequences represented in SEQ ID NOs: 10-30 with one or a plurality of amino acid residue(s) being conservatively replaced is also desirable for the antimicrobial peptide of the present invention.

Among the antimicrobial peptides described in the present specification, those having relatively short peptide chain can be easily produced according to a general chemosynthetic method. For example, either a conventionally known solid-phase synthetic method or liquid-phase synthetic method can be used. A solid-phase synthetic method using Boc (t-butyloxycarbonyl) or Fmoc (9-fluorenylmethoxycarbonyl) as a protective group for the amino group is preferable. For the antimicrobial peptides of the present invention, peptide chain having a desired amino acid sequence and a modified (e.g., C-terminal amidated) portion can be easily synthesized by a solid-phase synthetic method using a commercially available peptide synthesis apparatus (available from PerSeptive Biosystems, Applied Biosystems or the like).

Alternatively, the antimicrobial peptides of the present invention can be synthesized biologically based on a genetic engineering approach. This approach is preferable in producing a polypeptide having a relatively long peptide chain. In other words, DNA of a nucleotide sequence (including ATG start codon) that encodes the amino acid sequence of a desired antimicrobial peptide is synthesized. A recombinant vector having a gene construction substance for expression including this DNA and various regulatory elements (including promoter, ribosome binding site, terminator, enhancer, various cis-elements for controlling the expression level) is constructed in accordance with the host cell.

This recombinant vector is transduced into a predetermined host cell (e.g., yeast, insect cell, plant cell, animal (mammalian) cell) by a regular technique, and tissues or organisms including the host cell or the cell are cultured under predetermined conditions. Thus, a desired polypeptide can be expressed and produced in the cell. Then, a polypeptide is isolated from the host cell (from a medium when secreted) and purified, so that a desired antimicrobial peptide can be obtained.

Regarding methods for constructing the recombinant vector and methods for transducing the constructed recombinant vector into the host cell, conventional methods in this field can be utilized, and since such methods are not specific features of the present invention, detail descriptions will be omitted.

For example, a fusion protein expression system can be utilized for efficient mass production in a host cell. In other words, a gene (DNA) encoding an amino acid sequence of a desired antimicrobial peptide is chemically synthesized, and the synthesized gene is introduced into a preferred site of a suitable vector for expression of a fusion protein (e.g., a vector for expression of GST (Glutathione S-transferase) fusion protein such as pET series provided by Novagen and pGEX series provided by Amersham Bioscience). Then, the host cell (typically *E. coli*) is transformed by the vector. The obtained transformant is cultured so that a desired fusion protein is prepared. Then, the protein is extracted and purified. Then, the obtained purified fusion protein is cleaved by a predetermined enzyme (protease) and the separated desired peptide fragment (designed antimicrobial peptide) is collected by an affinity chromatography or the like. The antimicrobial peptide of the present invention can be produced by using such a conventionally known system for expression of a fusion protein (e.g., GST/His system provided by Amersham Bioscience can be utilized).

Alternatively, a template DNA for a cell-free protein synthesis system (i.e., synthesized gene fragment including a nucleotide sequence encoding an amino acid sequence of an antimicrobial peptide) is constructed, and various compounds (ATP, RNA polymerase, amino acids and the like) are used, so that a targeted polypeptide can be synthesized in vitro by using a so-called cell-free protein synthesis system. Regarding the cell-free protein synthesis system, for example, an article by Shimizu et al. (Shimizu et al., *Nature Biotechnology*, 19, 751-755 (2001)), an article by Madin et al. (Madin et al., *Proc. Natl. Acad. Sci. USA*, 97(2), 559-564 (2000)) can be referred to. At the time of filing the present application, a large number of enterprises have already been entrusted with production of polypeptide based on the technologies described in these articles, and kits for cell-free protein synthesis (e.g., PROTEIOS (trademark) Wheat germ cell-free protein synthesis kit available from TOYOBO Co., Ltd. in Japan) are commercially available.

Therefore, once an amino acid sequence of an antimicrobial peptide is determined/designed as described above, a desired antimicrobial peptide can be easily produced by a cell-free protein synthesis system according to the amino acid sequence. For example, the antimicrobial peptide can be easily produced based on PURESYSTEM (registered trademark) of POST GENOME INSTITUTE CO. LTD. in Japan.

A polynucleotide of a single strand or a double strand including a nucleotide sequence encoding the antimicrobial peptide of the present invention and/or a nucleotide sequence complementary to said sequence can be produced (synthesized) by a conventionally known method. In other words, a nucleotide sequence corresponding to the amino acid sequence of the antimicrobial peptide can be easily determined and provided by selecting a codon corresponding to each amino acid residue constituting the designed amino acid sequence. Then, once the nucleotide sequence is determined, then a polynucleotide (single strand) corresponding to the desired nucleotide sequence can be easily obtained by utilizing a DNA synthesis machine or the like. Furthermore, a targeted double strand DNA can be obtained by using various enzymatic synthesis means (typically PCR), using the obtained single strand as a template.

The polynucleotide provided by the present invention can be in the form of DNA or RNA (mRNA or the like). The DNA can be provided in the form of a double strand or a single strand. When it is provided in the form of a single strand, it can be in the form of a code chain (sense chain) or a non-code chain (anti-sense chain) complementary thereto.

As described above, the polynucleotide provided by the present invention can be used as a material for constructing a recombinant gene (expression cassette) for producing an antimicrobial peptide in various host cells or cell-free protein synthesis systems.

Several of the polynucleotides provided by the present invention encode an antimicrobial peptide that contains a novel amino acid sequence.

For example, an artificially designed polynucleotide that does not occur naturally, encoding a peptide chain composed of 100 or less (desirably 50 or less, and particularly desirably 20 or less) amino acid residues is provided. Such polynucleotide includes (or is substantially composed of) a nucleotide sequence encoding an amino acid sequence and/or a nucleotide sequence complementary to said sequence, while said amino acid sequence includes an amino acid sequence shown in SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30, or an amino acid sequence formed by conservatively replacing one or a plurality of amino acid residue(s) (for example, 2 to 3).

In addition, another artificially designed polynucleotide that does not occur naturally is also provided. Such artificially designed polynucleotide includes (or is substantially composed of) a nucleotide sequence encoding an amino acid sequence and/or a nucleotide sequence complementary to said sequence, while said nucleotide sequence encodes an antimicrobial peptide substantially composed of an amino acid sequence shown in SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30, or an amino acid sequence formed by conservatively replacing one or a plurality of amino acid residue(s) (for example, 2 to 3).

The antimicrobial peptide of the present invention has a high antimicrobial activity, and preferably has a relatively broad antimicrobial spectrum, and can be used as the main component of an antimicrobial agent. For example, it can be used for the purpose of treating bacterial infection, sanitizing an external injury, preventing eye diseases, cleaning an oral cavity (gargling), preventing decay of foods, retaining freshness, removing odor, bacteriocide or bacteriostat for the surface of furniture or sanitary equipment and the like.

Apart from the antimicrobial peptide, the antimicrobial agent can also includes, as a secondary component, various filling agents, fillers, binders, moisturizers, surfactants, excipients, pigments, fragrances or the like can be used, depending on the use or the form of the antimicrobial agent.

There is no particular limitation regarding the form of the antimicrobial agent. For example, examples of a typical form of medicines for internal or external use include ointment, liquid medicine, suspension, emulsion, aerosol, foam, granule, powder, tablet, and capsule. Furthermore, in order to use it for injection, it can be produced in the form of a freeze dried substance or a granulated substance that is to be dissolved in a physiological saline or a buffering solution (for example PBS) or the like immediately before use so as to prepare a medical fluid.

The process itself in which various forms of pharmaceuticals are prepared using materials including the antimicrobial peptide (main component) and various carriers (secondary component) can be performed according to a conventionally known method, and this does not characterize the present invention so that the detailed description thereof will be omitted. As a detailed information source for prescription, for example, "Comprehensive Medicinal Chemistry" edited by Corwin Hansch and published by Pergamon Press (1990) can be referred to.

The antimicrobial agent provided by the present invention can be used by a method or a dose in accordance with the form and the purpose thereof.

The antimicrobial peptide described in the present specification can maintain a high antimicrobial activity even under a condition where relatively high concentration of saline (for example sodium chloride) or organic compound such as serum is present. Hence usage in situations where saline or serum is present is also preferable. For example, the antimicrobial agent provided by the present invention can be administered, as a liquid agent, intravenously, intramuscularly, subcutaneous, intracutaneous or intraperitoneal injection, or by enema to a patient.

Alternatively, the agent can be administered orally when it is in a solid form such as a tablet. When it is used for the purpose of sanitizing (sterilizing) the surface of sanitary ceramic ware or preventing decay of foods, a liquid agent containing a relatively large amount (e.g., 1 to 100 mg/ml) of peptide can be sprayed directly onto the surface of a targeted object, or the surface of a targeted object can be wiped with fabric or paper impregnated with the liquid agent. These are only examples, and the same form and usage as those of conventional peptide antibiotics, agricultural chemicals, medicated cosmetics or the like having a peptide as a component can be applied.

For example, for cancer patients that are subjected to radiotherapy or aids patients, prevention and treatment of bacterial infection are important concerns. The antimicrobial peptide described in the present specification can exhibit high antimicrobial effect against bacteria responsible for infectious diseases (for example *Staphylococcus aureus*). Therefore, the antimicrobial peptide of the present invention is useful as a main component of an antimicrobial agent.

The polynucleotide encoding the antimicrobial peptide of the present invention can be used as a material for so-called gene therapy. For example, a gene (typically DNA segment, or RNA segment) encoding the antimicrobial peptide is incorporated into a suitable vector, and transduced into a targeted site, so that the antimicrobial peptide related to the present invention can be expressed constantly in an organism (cell). Therefore, the polynucleotide (DNA segment, RNA segment or the like) encoding the antimicrobial peptide of the present invention is useful as a pharmaceutical for preventing or treating bacterial infection to the above-described patients or the like.

It is important to prevent bacterial infection during culture of skin, bone or various organs in the field of regenerative medicine. The antimicrobial peptide described in the present specification has a very low toxicity with respect to the mammal cells or tissues (see the example described hereinafter) and exhibits an antimicrobial effect selectively with respect to the bacterium. Therefore, this is very useful as a pharmaceutical for preventing bacterial infection of a cultured organ or the like. For example, as shown in the examples later, bacterial infection of an organ during culture can be prevented by adding solely the antimicrobial peptide or an antimicrobial agent having the peptide as one of the main components in an appropriate concentration in a culture solution.

Furthermore, with respect to cultured cells or cultured tissues, the polynucleotide encoding the antimicrobial peptide of the present invention can be used as a material used for gene therapy. For example, a gene (typically DNA segment, or RNA segment) encoding the antimicrobial peptide of the present invention is incorporated into a suitable vector, and transduced into a targeted cultured tissue, so that the antimicrobial peptide related to the present invention can be expressed constantly or in a desired period in a cultured tissue (or cell). Therefore, the polynucleotide (DNA segment, RNA segment or the like) encoding the antimicrobial peptide of the present invention is useful as a pharmaceutical for preventing or treating bacterial infection of cultured tissues.

Hereinafter, several examples of the present invention will be described, but they are not intended to limit the present invention.

EXAMPLE 1

Synthesis of Antimicrobial Peptides 27 types of polypeptide (samples 1 to 21, comparative samples 1 to 7) were produced with a peptide synthesis machine that will be described hereinafter. Table 1 shows the amino acid sequences of these polypeptides.

TABLE 1

| Sample No. | Amino Acid Sequence | Total Number of Amino Acid Residues |
|---|---|---|
| sample 1 | RKKKRKV<u>LMWWML</u>R-$_{CONH2}$ (SEQ ID NO: 10) | 14 |
| sample 2 | RKKKRKV<u>LMWWML</u>-$_{CONH2}$ (SEQ ID NO: 11) | 13 |
| sample 3 | RIRKKLR<u>LMWWML</u>-$_{CONH2}$ (SEQ ID NO: 12) | 13 |
| sample 4 | <u>LMWWML</u>RIRKKLR-$_{CONH2}$ (SEQ ID NO: 13) | 13 |
| sample 5 | <u>LMWWML</u>RKKKRKV-$_{CONH2}$ (SEQ ID NO: 14) | 13 |
| sample 6 | RKKKRKV<u>LMWWML</u>AR-$_{CONH2}$ (SEQ ID NO: 15) | 15 |
| sample 7 | RIRKKLR<u>LMWWML</u>AR-$_{CONH2}$ (SEQ ID NO: 16) | 15 |
| sample 8 | $_{Ac-}$RKKKRKV<u>LMWWML</u>R-$_{CONH2}$ (SEQ ID NO: 17) | 14 |
| sample 9 | RKKKRKV<u>VVYWLL</u>R-$_{CONH2}$ (SEQ ID NO: 18) | 14 |
| sample 10 | RKKKRKV<u>LLTAKM</u>R-$_{CONH2}$ (SEQ ID NO: 19) | 14 |
| sample 11 | RKKKRKV<u>FFYMVI</u>R-$_{CONH2}$ (SEQ ID NO: 20) | 14 |
| sample 12 | RKKKRKV<u>LYLGAV</u>R-$_{CONH2}$ (SEQ ID NO: 21) | 14 |
| sample 13 | RKRKRKR<u>LMWWML</u>-$_{CONH2}$ (SEQ ID NO: 22) | 13 |
| sample 14 | RIRKKLR<u>LMWWML</u>R-$_{CONH2}$ (SEQ ID NO: 23) | 14 |
| sample 15 | LKRKLQR<u>LMWWML</u>-$_{CONH2}$ (SEQ ID NO: 24) | 13 |
| sample 16 | RKKKRKV<u>LMWWML</u>R-$_{COOH}$ (SEQ ID NO: 25) | 14 |
| sample 17 | RKRR<u>LMWWML</u>KKLR-$_{CONH2}$ (SEQ ID NO: 26) | 14 |
| sample 18 | LKRKLQR<u>LMWWML</u>R-$_{CONH2}$ (SEQ ID NO: 27) | 14 |
| sample 19 | RKKRRQRRR<u>LMWWML</u>-$_{CONH2}$ (SEQ ID NO: 28) | 15 |
| sample 20 | <u>LMWWML</u>RIRKKLRVGR-$_{CONH2}$ (SEQ ID NO: 29) | 16 |
| sample 21 | RKKKRKV<u>LMWWML</u>KPV-CONH2 (SEQ ID NO: 30) | 16 |
| sample 22 | LKRKLQR<u>VVYWLL</u>-$_{CONH2}$ (SEQ ID NO: 38) | 13 |

TABLE 1-continued

| Sample No. | Amino Acid Sequence | Total Number of Amino Acid Residues |
|---|---|---|
| comparative sample 1 | RGDLMWWMLAR-$_{CONH2}$ (SEQ ID NO: 31) | 11 |
| comparative sample 2 | TGTG-$_{CONH2}$ (SEQ ID NO: 32) | 4 |
| comparative sample 3 | LMWWML-$_{CONH2}$ (SEQ ID NO: 33) | 6 |
| comparative sample 4 | RAVTLYLGAVAA-$_{CONH2}$ (SEQ ID NO: 34) | 12 |
| comparative sample 5 | RLLTAKMLMWWMLR-$_{CONH2}$ (SEQ ID NO: 35) | 14 |
| comparative sample 6 | RIRKKLRYIGSR-$_{CONH2}$ (SEQ ID NO: 36) | 12 |
| comparative sample 7 | RKKKRKVYIGSR-$_{CONH2}$ (SEQ ID NO: 37) | 12 |

As illustrated in Table 1, samples 1 to 21 each includes an LBS sequence (underlined portions in Table 1) composed of 6 amino acid residues shown in either one of SEQ ID NO: 1-9. Further, samples 1 to 21 also each includes antimicrobial associated sequence composed of 4 to 10 amino acid residues linked in tandem to the C-terminal and/or N-terminal of such LBS sequence, and such antimicrobial associated sequences are shown in italic in Table 1. More specifically, samples 1, 2, 3, 6, 7, 8, 9, 10, 11, 12, 13, 14, 15, 16, 17, 18, 19 and 21 include high basic partial sequence composed of 4 to 9 amino acid residues at the N-terminal of the LBS sequence. Samples 4, 5, 17 and 20 include high basic partial sequence composed of 4 to 9 amino acid residues at the C-terminal of the LBS sequence. Among these samples, sample 17 includes high basic partial sequence composed of 4 amino acid residues at both the C- and N-terminals of the LBS sequence respectively. Further, although sample 20 includes high basic partial sequence composed of 10 amino acid residues at the C-terminal of the LBS sequence, the 3 amino acid residues "VGR" at the C-terminal corresponds to the C-terminal sequence of the known antimicrobial peptide "protegrin-1", and is also an amino acid sequence related to the present example that can express antimicrobial activity against at least one kind of bacteria or fungi. In addition, sample 21 includes 3 amino acid residues "KPV" at the C-terminal of the LBS sequence. Such KPV sequence corresponds to the C-terminal sequence of "alpha-MSH", and is a preferable example of an amino acid sequence that can express antimicrobial activity against at least 1 kind of bacteria or fungi.

In samples 1, 6, 7, 8, 9, 10, 11, 12, 14, 16 and 18, one or two amino acid residue(s) that is neither an LBS sequence nor an antimicrobial associated sequence is added to the C-terminal of the peptide chain. Generally, antimicrobial activity can be improved by adding R to the C-terminal of the peptide chain.

On the contrary, comparative sample 1 is a peptide composed of 11 amino acid residues including LBS sequence (SEQ ID NO: 1) but not antimicrobial associated sequence. Comparative sample 2 is a peptide composed of 4 amino acid residues including neither LBS sequence nor antimicrobial associated sequence. Comparative sample 3 is a peptide composed of 6 amino acid residues composed exclusively of LBS sequence (SEQ ID NO: 1). Comparative sample 4 is a peptide composed of 12 amino acid residues including LBS sequence (SEQ ID NO: 6) but not antimicrobial associated sequence. Comparative sample 5 is a peptide composed of 14 amino acid residues including two LBS sequences (SEQ ID NOs: 1 and 9) linked in tandem but not antimicrobial associated sequence. Comparative samples 6 and 7 are respectively peptide composed of 12 amino acid residues including antimicrobial associated sequence (high basic partial sequence) but not LBS sequence.

As illustrated in Table 1, apart from sample 16, the carboxyl group (—COOH) of the C-terminal amino acid is amidated (—CONH$_2$). In addition, the amino group of the N-terminal in sample 8 is acetylated (—Ac).

The above-described polypeptides (each includes 20 or less amino acid residue(s)) were synthesized by a solid synthesis method (Fmoc method) using a commercially available peptide synthesis machine (PEPTIDE SYNTHESIZER 9050 manufactured by PerSeptive Biosystems). As a condensing agent, HATU (Applied Biosystems product) was used, and the resin and the amino acids used in the solid synthesis method were purchased from NOVA biochem. To amidate the C-terminal of the amino acid sequence, "Rink Amide resin (100 to 200 mesh)" was used as the solid carrier.

Therefore, a peptide chain is elongated from Fmoc-amino acid that is bound to a resin by repeating deprotection reaction and condensation reaction according to the synthesis program of the above-described peptide synthesizing machine, so that a synthesized peptide of a targeted length was obtained. More specifically, Fmoc, which is an amino protecting group of an amino acid, is cleaved and removed with 20% piperidine/dimethylformamide (DMF) (peptide synthesis grade manufactured by KANTO KAGAKU), cleaned with DMF, reacted with 4 eq of Fmoc-amino acid (—OH) each, and cleaned with DMF. This operation was repeated. Then, after all the elongation reaction of the peptide chain was completed, the Fmoc group was cleaved with 20% piperidine/DMF, and the above-described reaction product was cleaned with DMF and methanol in this order.

After solid synthesis, the synthesized peptide chain and the resin were both transferred to a centrifuge tube, and 1.8 mL of ethanediol, 0.6 mL of m-cresol, 3.6 mL of thioanisole, and 24 mL of trifluoroacetic acid were added thereto, and then the mixture was stirred at room temperature for 2 hours. Thereafter, resin bound to the peptide chain was filtrated and removed.

Then, cooled ethanol was added to the filtrate, and a peptide precipitate was obtained by cooling with iced water. Thereafter, the supernatant was discarded by centrifugation (for five minutes at 2500 rpm). Cool diethyl ether was again added to the precipitate and stirred sufficiently, and then centrifugation was performed in the same conditions as above. This process of stirring and centrifugation was repeated in total of three.

The obtained peptide precipitate was vacuum-dried and purified with a high speed liquid chromatography (Waters 600 manufactured by Waters Corp.).

More specifically, pre-column (Guard-Pak Delta-pak C18 A300 manufactured by Nippon Waters) and C18 reverse phase column (XTerra (registered trademark) column, MS C18, 5 µm, 4.6×150 mm manufactured by Nippon Waters) were used, and a mixed solution of 0.1% trifluoroacetic acid aqueous solution and 0.1% trifluoroacetic acid acetonitrile solution was used as an eluent. In other words, separation and purification were performed for 30 to 40 minutes using the above-described columns at a flow rate of 1.5 mL/min while increasing over time the amount of the trifluoroacetic acid acetonitrile solution contained in the eluent (providing the concentration gradient from 10% to 80% in volume ratio). The peptide eluted from the reverse phase column was detected at a wavelength of 220 nm using an ultraviolet ray detector (490E Detector manufactured by Waters) and shown on a recording chart as the peaks.

The molecular weight of each eluted peptide was determined, using Voyager DE RP (trademark) manufactured by PerSeptive Biosystems, based on MALDI-TOF MS (Matrix-Assisted Laser Desorption Time of Flight Mass Spectrometry). As a result, it was confirmed that the targeted peptide was synthesized and purified.

EXAMPLE 2

Antimicrobial Activity of Synthesized Peptides (1)

Regarding the antimicrobial peptide (samples 1 to 20) related to the present invention, the antimicrobial activities (minimum inhibitory concentration: MIC) with respect to gram-negative bacteria (*Escherichia coli* IFO 3972) and gram-positive bacteria (*Staphylococcus aureus* IFO 12732) were determined by a liquid medium dilution technique using a 96-well microplate.

First, a drug (synthesized polypeptide) solution having a concentration of 40 times of the highest test concentration was prepared using sterile distilled water, and liquid-bouillon mediums (more specifically, "Mueller Hinton Broth" manufactured by DIFCO) including cation and having drug concentrations of 100, 50, 25, 12.5, 6.3, 3.1, 1.6 and 0.8 µM were respectively produced. The cation included was prepared as follows: dissolving 3.68 g of $CaCl_2.2H_2O$ in 100 mL of purified water (10 mg.$Ca^{2+}$/mL), and thereafter adding 500 µL thereof into 100 mL of Mueller Hinton Broth; and dissolving 8.36 g of $MgCl_2.6H_2O$ in 100 mL of purified water (10 mg.$Mg^{2+}$/mL), and thereafter adding 250 µL thereof into 100 mL of Mueller Hinton Broth. Thereafter, the produced liquid-bouillon mediums including the drug of each concentration were then fed to the 96-well microplate at 100 mL a time.

At the same time, test bacteria cultured for 18 hours at 37° C. on an agar plate ("Muller Hinton Agar" manufactured by DIFCO) were gathered by scratching with a loop, and then suspended in a sterilized physiological saline. Bacterial suspension 5 µL prepared at an equivalent of $2 \times 10^7$ cells/mL was respectively inoculated (number of bacteria to be tested: approximately $1 \times 10^6$ cells/mL) onto the drug solution and fed to each well of the above-described microplate. After inoculation, the microplate was then incubated in an incubator at 37° C., and the presence of bacteria was evaluated based on the turbidity 24 hours later. The minimum drug concentration (polypeptide concentration), in which an increased in turbidity caused by bacteria was not detected at the time of measurement, was defined as MIC (minimum inhibitory concentration) (unit: µM) in the present embodiment. The results are illustrated in Table 2. In addition, MIC were determined in the same manner using polymyxin B as a comparison.

TABLE 2

| | Antimicrobial Activities (MIC: µM) | |
|---|---|---|
| Sample No. | E. coli | S. aureus |
| sample 1 | 6.3 | 3.1 |
| sample 2 | 12.5 | 3.1 |
| sample 3 | 6.3 | 3.1 |
| sample 4 | 6.3 | 3.1 |
| sample 5 | 50 | 3.1 |

TABLE 2-continued

| | Antimicrobial Activities (MIC: µM) | |
|---|---|---|
| Sample No. | E. coli | S. aureus |
| sample 6 | 12.5 | 6.3 |
| sample 7 | 6.3 | 3.1 |
| sample 8 | 12.5 | 3.1 |
| sample 9 | 12.5 | 3.1 |
| sample 10 | 50 | 12.5 |
| sample 11 | 6.3 | 3.1 |
| sample 12 | 50 | 12.5 |
| sample 13 | 6.3 | 3.1 |
| sample 14 | 6.3 | 3.1 |
| sample 15 | 12.5 | 3.1 |
| sample 16 | 12.5 | 3.1 |
| sample 17 | 6.3 | 3.1 |
| sample 18 | 12.5 | 6.3 |
| sample 19 | 12.5 | 6.3 |
| sample 20 | 6.3 | 3.1 |
| comparative sample 1 | >100 | >100 |
| comparative sample 2 | >100 | >100 |
| comparative sample 3 | >100 | >100 |
| comparative sample 4 | >100 | >100 |
| comparative sample 5 | >100 | 12.5 |
| comparative sample 6 | >100 | 50 |
| comparative sample 7 | 100 | 12.5 |
| polymyxin B | 1.6 | 6.3 |

As clearly illustrated in the results shown in Table 2, all the polypeptides related to the present invention (samples 1 to 20) exhibited high antimicrobial activities as compared to the comparative polypeptides (comparative samples 1 to 7).

Specifically, high antimicrobial activities were identified in the polypeptide including palindrome sequence "LMW-WML", which is an LBS sequence, represented by SEQ ID NO: 1. In addition, polypeptide of which C-terminal was amidated (sample 1) exhibited higher antimicrobial activities than polypeptide having the same sequence but of which C-terminal was not amidated (sample 16). According to the results shown in Table 2, it had been verified that antimicrobial peptides of the present invention had an excellent antimicrobial activity and a wider antimicrobial spectrum.

EXAMPLE 3

Antimicrobial Activity of Synthesized Peptides (2)

Next, the antimicrobial activities (MIC) against gram-positive bacteria (*S. aureus*) in the presence of serum were tested with the same method as Example 2. More specifically, a drug (synthesized polypeptide) solution having a concentration of 40 times of the highest test concentration was first prepared using sterile distilled water, and liquid-bouillon mediums ("Mueller Hinton Broth" with cation prepared in advance, which is the same as Example 2) having drug concentrations of 50, 25, 12.5, 6.3, 3.1, 1.6 and 0.8 µM, and with horse serum (mechanically sterilized Nippon Biotest Laboratories inc. product) added therein such that the horse serum had a mass ratio of 10%, 20% or 50% of the entire medium, were respectively produced. Thereafter, the produced liquid-bouillon mediums including the drug and the serum of each concentration were then fed to the 96-well microplate at 100 mL a time, and MIC were determined by the method same as Example 2. The results are shown in Table 3. Sample X in the table is a mixture of sample 1 and sample 16 based on a mass ratio of 1:1. "-" in the table indicate "untested".

As clearly illustrated in the results shown in Table 3, it had been verified that, as compared to the comparative polypeptide, the polypeptides of the present invention could maintained a high antimicrobial activities even in the presence of serum. Therefore, the antimicrobial peptide of the present invention is also preferable to be used in strains (for example, blood) in which a relatively high quantity of organic matter such as serum is present. Sample 21, which includes LBS sequence, and as antimicrobial associated sequence, both amino acid sequence (in this case KPV sequence) and high basic partial sequence that can express antimicrobial activity against at least one kind of bacteria or fungi, exhibits particularly high antimicrobial activity.

TABLE 3

Antimicrobial Activities (MIC: μM) against *S. aureus*

| | horse serum concentration | | |
|---|---|---|---|
| | 10% | 20% | 50% |
| sample 1 | 3.1 | 3.1 | 3.1 |
| sample 3 | 3.1 | — | — |
| sample 4 | 6.3 | — | — |
| sample 6 | 3.1 | 3.1 | 1.6 |
| sample 7 | 3.1 | 6.3 | 6.3 |
| sample 8 | 3.1 | — | 6.3 |
| sample 14 | 6.3 | — | — |
| sample 15 | 6.3 | — | — |
| sample 16 | 3.1 | — | — |
| sample 21 | 1.6 | — | — |
| sample X | 6.3 | — | — |
| comparative sample 1 | >50 | — | — |
| polymyxin B | 6.3 | 6.3 | 3.1 |

EXAMPLE 4

Antimicrobial Activity of Synthesized Peptides (3)

Antimicrobial activity against fungi (*Aspergillus niger* IFO 6341) of the antimicrobial peptides related to the present invention was tested according to a general antimycotic susceptibility test as follows.

More specifically, a slant or plate medium ("potato dextrose agar" medium manufactured by DIFCO was used typically) adhered with spores (conidia) was prepared in advance, and *A. niger* (IFO 6341; JIS test strain) were gathered from the medium by scratching the medium surface 4 to 5 times from bottom up with a 1 μL disposable loop and suspended in 25 mL of PBS (free of Mg, Ca) solution containing 0.05% of surfactant (Tween® 80). Thereafter, pipetting was performed using a measuring pipette or the like such that clusters of black spores disappeared completely. The spore concentration of the spore suspension prepared by such method was determined using a hemocytometer while the above-described surfactant containing PBS solution was being diluted accordingly, thereby deriving a spore suspension having a spore concentration of approximately $2.5 \times 10^5$ spores/mL.

At the same time, the above-described two polypeptides (samples 1, 3) and benzalkonium chloride serving as a comparison for antimycotic activity were dissolved in 10 mM of HEPES buffer (pH7.0) respectively to prepare stock solutions with a 2.0 mg/mL drug concentration. These were sequentially diluted to prepare various kinds of test drugs with drug (each polypeptide or benzalkonium chloride) concentrations of 400, 200, 100, 50, 25, 5 and 0.5 μg/mL.

A spore germination inhibition test and a spore growth inhibition test were performed using the above-prepared drugs and spore suspension as follows.

First, each of the above-described drugs was fed to the 96-well microplate at 40 μL a time for the spore germination inhibition test. The surplus drugs were stored in a refrigerator (4° C.) to be used for the spore growth inhibition test to be perform at a later date.

Next, a test fungus suspension was prepared by adding, with respect to 10 part by mass of the above-described spore suspension, 2 parts by mass of Alamar Blue fluorescence reagent (product of Wako Pure Chemical Industries, Ltd.) and 8 parts by mass of RPMI1640 medium containing 0.165M of MOPS, which was prepared by dissolving 5.2 g of RPMI1640 (product of Irvine Scientific) and 1.0 g of NaHCO$_3$ in 450 mL of sterile distilled water and thereafter adding 17.12 g of MOPS and stirring, and adjusting the pH value to 7.0 by adding NaOH, and then filling up to 500 mL by adding sterile distilled water. Then, the fungus suspension was fed at 160 μL a time to the wells in which the above-described drugs were added. In addition, empty wells in which no drug was added were also fed at 160 μL a time for spore growth inhibition test. After feeding, it was cultured under a humid environment for 16 hours in an incubator at 30° C.

Sixteen hours after the beginning of culturing, the plate was retrieve from the incubator, and the presence of generation (growth) of mycelia in each well (well that had already been fed exclusively by the above-described test drug) used for spore growth inhibition test was evaluated with a microscope. With regard to well(s) in which mycelia generation (growth) was determined, either one of the above-described drugs stored in the refrigerator was fed at 40 μL a time. After feeding, the plate was returned into the incubator at 30° C. and continued to be culture under a humid environment.

Twenty-four hours and 48 hours after the beginning of culturing, the colour of the mediums in the wells used for spore germination inhibition test and the wells for spore growth inhibition test were observed. Here, those in which the Alamar Blue included within the medium remain blue (oxidized form) were evaluated as positive of antimicrobial activity positive, and those that are pink (reduced form) were evaluated as negative of antimicrobial activity. Moreover, the smallest drug concentration recognized as oxidized form (blue color) was served as MIC (minimum growth inhibitory concentration) in the spore germination inhibition test and the spore growth inhibition test related to the present example. The results are illustrated in Table 4.

TABLE 4

Antimicrobial Activities against *A. niger* (MIC: μg/mL)

| | spore germination inhibition test | | spore growth inhibition test |
|---|---|---|---|
| | after 24 hours | after 48 hours | after 24 hours |
| sample 1 | 50 | 50 | 100 |
| sample 3 | 100 | 100 | 100 |
| benzalkonium chloride | 25 | 25 | 25 |

As clearly illustrated in the results shown in Table 4, it had been verified that the peptides related to the present invention could exhibit high antimicrobial activities even against fungi (mould, yeast) such as *A. niger*. Therefore, an antifungal agent including any of the antimicrobial peptide described in the present specification as a main component is provided by the present invention for in vivo or ex vivo usage.

EXAMPLE 5

Preparation of Granules

After 50 mg of polypeptide from sample 1 were mixed with 50 mg of crystallized cellulose and 400 mg of lactose, 1 mL of a mixed solution of ethanol and water was added and the mixture was kneaded. This kneaded product was granulated according to a regular method, and thus a granule (antimicrobial granule) having the antimicrobial peptide as the main component was obtained.

EXAMPLE 6

Treatment Effect Test on Mice

A polypeptide (sample 22) composed of 13 amino acid residues and with an amino acid sequence of LKRKLQRV-VYWLL was synthesized by the process same as Example 1. The carboxyl group (—COOH) of the amino acid at the C-terminal of the polypeptide was amidated (—CONH$_2$).

Further, as clearly illustrated in the amino acid sequence, the sequence "VVYWLL" on the C-terminal side of the synthesized polypeptide (sample 22) constitutes the LBS sequence same as sample 9, and the sequence "LKRKLQR" on the N-terminal side constitute the antimicrobial associated sequence (high basic partial sequence) same as samples 15 and 18.

The following test was performed to evaluate the treatment effect on mice infected by bacterial (MRSA) of sample 22 obtained by synthesis.

Mice (ICR, SLC, male, 5 weeks old) were prepared by rearing on drinking water mixed with amphotericin B (AMPH: product of Bristol-Myers Company) and tetracycline, such that their concentrations are 10 μg/mL (AMPH) and 2000 μg/mL (tetracycline) respectively, a week before the start of the test, and the immunity of the mice was weaken by administrating 200 mg/kg amount of cyclophosphamide into the abdominal for 3 days from the fourth day prior to the test.

Bacterial suspension prepared by suspending methicillin-resistant *Staphylococcus aureus* (MRSA, No. 164 strain) in 10% (w/v) of mucin solution was orally administered to the mice at a bacterial administration quantity of $10^8$ cells/mouse, thereby eliciting MRSA infection.

One hour after the bacterial inoculation, antimicrobial agent prepared by suspending the test material (therefore polypeptide of sample 22) in 10% of gum arabic solution was orally administered. The administered quantity of suspension was 100 mg/kg. A total of 5 test groups, with each test group containing 5 test mice, were tested. For comparison, antimicrobial agent prepared by suspending vancomycin in 10% of gum arabic solution was orally administered to the test mice under the same conditions.

After the drug administration, test mice were slaughtered approximately 24 hours later, and the contents in the intestine extracted, and the bacterial count of MRSA examined. More specifically, 1.8 mL of physiological saline was added to and mixed with approximately 0.2 g of intestine contents. A fixed quantity of such mixture was smeared on mannitol agar medium (product of Nissui Pharmaceutical Co., Ltd) including gentamicin (GM) with a concentration of 20 μm/mL, and cultured for 3 days at 37° C. The bacterial count appeared on the medium was counted, and the results shown in Table 5.

As clearly illustrated in the results shown in Table 5, the drug including the polypeptide of sample 22 related to this example exhibited the same effect as the drug including vancomycin and serving as a comparison.

TABLE 5

MRSA bacterial quantity ($\times 10^3$ cells/g) in intestine content of each administered group

| | Administered group | | | | | |
|---|---|---|---|---|---|---|
| | 1 | 2 | 3 | 4 | 5 | Average |
| Sample 22 | 36 | 35 | 30 | 16 | 26 | 29 |
| Vancomycin | 8 | 10 | 43 | 22 | 26 | 22 |

*) drug administered quantity: 100 mg/kg

Specific examples of the present invention have been described above, but they are only illustrative and not limiting the scope of the claims. All changes and modifications from the specific examples illustrated above are intended to be embraced in the techniques disclosed in the appended claims.

The technical elements described in the specification or the drawings can exhibit technical usefulness, either alone or in combination, and combinations are not limited to those described in the claims as filed. The techniques illustrated in the specification or the drawings can achieve a plurality of purposes at the same time, and achieving only one of them has technical usefulness.

What is claimed is:

1. An artificially designed antimicrobial peptide that does not occur naturally, wherein the antimicrobial peptide includes a sequence composed of at least 6 contiguous amino acid residues selected from the group consisting of LMWWML (SEQ. ID. NO: 1), LMWWLL (SEQ. ID. NO: 2), CLFWLL (SEQ. ID. NO: 3), LIWYLL (SEQ. ID. NO: 4), VVYWLL (SEQ. ID. NO: 5), LYLGAV (SEQ. ID. NO: 6), LITSKM (SEQ. ID. NO: 7), FFYMVI (SEQ. ID. NO: 8), AND LLTAKM (SEQ. ID. NO: 9), as an amino acid sequence constituting laminin biding site (LBS), a partial sequence linked in tandem to the N-terminal and/or C-terminal of said sequence, where the partial sequence is a high basic partial sequence and more than half of the amino acid residues constituting the partial sequence composed of 3 or more contiguous amino residues are lysine or arginine, wherein the total number of amino acid residues is 20 or less.

2. The antimicrobial peptide according to claim 1 including an amino acid sequence shown in any one of SEQ ID NOs: 10-30 or said sequence with one, two, or three amino acid residue(s) conservatively replaced.

3. The antimicrobial peptide of claim 1, wherein at least one amino acid residue is amidated.

4. An antimicrobial agent comprising the antimicrobial peptide of claim 1, and a pharmaceutically acceptable carrier.

* * * * *

SEQUENCE LISTING

<160> NUMBER OF SEQ ID NOS: 38

<210> SEQ ID NO 1
<211> LENGTH: 6
<212> TYPE: PRT
<213> ORGANISM: Homo sapiens

<400> SEQUENCE: 1

Leu Met Trp Trp Met Leu
1               5

<210> SEQ ID NO 2
<211> LENGTH: 6
<212> TYPE: PRT
<213> ORGANISM: Drosophila melanogaster

```
<400> SEQUENCE: 2

Leu Met Trp Trp Leu Leu
1               5

<210> SEQ ID NO 3
<211> LENGTH: 6
<212> TYPE: PRT
<213> ORGANISM: Arabidopsis thaliana

<400> SEQUENCE: 3

Cys Leu Phe Trp Leu Leu
1               5

<210> SEQ ID NO 4
<211> LENGTH: 6
<212> TYPE: PRT
<213> ORGANISM: Saccharomyces cerevisiae

<400> SEQUENCE: 4

Leu Ile Trp Tyr Leu Leu
1               5

<210> SEQ ID NO 5
<211> LENGTH: 6
<212> TYPE: PRT
<213> ORGANISM: Haloarcula marismortui

<400> SEQUENCE: 5

Val Val Tyr Trp Leu Leu
1               5

<210> SEQ ID NO 6
<211> LENGTH: 6
<212> TYPE: PRT
<213> ORGANISM: Escherichia coli

<400> SEQUENCE: 6

Leu Tyr Leu Gly Ala Val
1               5

<210> SEQ ID NO 7
<211> LENGTH: 6
<212> TYPE: PRT
<213> ORGANISM: Pediococcus acidilactici

<400> SEQUENCE: 7

Leu Ile Thr Ser Lys Met
1               5

<210> SEQ ID NO 8
<211> LENGTH: 6
<212> TYPE: PRT
<213> ORGANISM: Acanthamoeba castellanii

<400> SEQUENCE: 8

Phe Phe Tyr Met Val Ile
1               5

<210> SEQ ID NO 9
<211> LENGTH: 6
<212> TYPE: PRT
<213> ORGANISM: Staphylococcus aureus

<400> SEQUENCE: 9
```

```
Leu Leu Thr Ala Lys Met
1               5
```

<210> SEQ ID NO 10
<211> LENGTH: 14
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 10

```
Arg Lys Lys Lys Arg Lys Val Leu Met Trp Trp Met Leu Arg
1               5                   10
```

<210> SEQ ID NO 11
<211> LENGTH: 13
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 11

```
Arg Lys Lys Lys Arg Lys Val Leu Met Trp Trp Met Leu
1               5                   10
```

<210> SEQ ID NO 12
<211> LENGTH: 13
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 12

```
Arg Ile Arg Lys Lys Leu Arg Leu Met Trp Trp Met Leu
1               5                   10
```

<210> SEQ ID NO 13
<211> LENGTH: 13
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 13

```
Leu Met Trp Trp Met Leu Arg Ile Arg Lys Lys Leu Arg
1               5                   10
```

<210> SEQ ID NO 14
<211> LENGTH: 13
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 14

```
Leu Met Trp Trp Met Leu Arg Lys Lys Lys Arg Lys Val
1               5                   10
```

<210> SEQ ID NO 15
<211> LENGTH: 15
<212> TYPE: PRT
<213> ORGANISM: Artificial Sequence
<220> FEATURE:

```
<223> OTHER INFORMATION: Designed antimicrobial peptide containing a
      terminal amide group

<400> SEQUENCE: 15

Arg Lys Lys Lys Arg Lys Val Leu Met Trp Trp Met Leu Ala Arg
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 16

Arg Ile Arg Lys Lys Leu Arg Leu Met Trp Trp Met Leu Ala Arg
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 17

Arg Lys Lys Lys Arg Lys Val Leu Met Trp Trp Met Leu Arg
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 18

Arg Lys Lys Lys Arg Lys Val Val Val Tyr Trp Leu Leu Arg
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 19

Arg Lys Lys Lys Arg Lys Val Leu Leu Thr Ala Lys Met Arg
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 20

Arg Lys Lys Lys Arg Lys Val Phe Phe Tyr Met Val Ile Arg
1               5                   10
```

```
<210> SEQ ID NO 21
<211> LENGTH: 14
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 21

Arg Lys Lys Lys Arg Lys Val Leu Tyr Leu Gly Ala Val Arg
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 22

Arg Lys Arg Lys Arg Lys Arg Leu Met Trp Trp Met Leu
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 23

Arg Ile Arg Lys Lys Leu Arg Leu Met Trp Trp Met Leu Arg
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 24

Leu Lys Arg Lys Leu Gln Arg Leu Met Trp Trp Met Leu
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Designed antimicrobial peptide

<400> SEQUENCE: 25

Arg Lys Lys Lys Arg Lys Val Leu Met Trp Trp Met Leu Arg
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 26
```

```
Arg Lys Arg Arg Leu Met Trp Trp Met Leu Lys Lys Leu Arg
1               5                   10
```

<210> SEQ ID NO 27
<211> LENGTH: 14
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 27

```
Leu Lys Arg Lys Leu Gln Arg Leu Met Trp Trp Met Leu Arg
1               5                   10
```

<210> SEQ ID NO 28
<211> LENGTH: 15
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 28

```
Arg Lys Lys Arg Arg Gln Arg Arg Arg Leu Met Trp Trp Met Leu
1               5                   10                  15
```

<210> SEQ ID NO 29
<211> LENGTH: 16
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 29

```
Leu Met Trp Trp Met Leu Arg Ile Arg Lys Lys Leu Arg Val Gly Arg
1               5                   10                  15
```

<210> SEQ ID NO 30
<211> LENGTH: 16
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 30

```
Arg Lys Lys Lys Arg Lys Val Leu Met Trp Trp Met Leu Lys Pro Val
1               5                   10                  15
```

<210> SEQ ID NO 31
<211> LENGTH: 11
<212> TYPE: PRT
<213> ORGANISM: Artificial Sequence
<220> FEATURE:
<223> OTHER INFORMATION: Designed peptide containing a terminal amide
      group

<400> SEQUENCE: 31

```
Arg Gly Asp Leu Met Trp Trp Met Leu Ala Arg
1               5                   10
```

<210> SEQ ID NO 32
<211> LENGTH: 4
<212> TYPE: PRT
<213> ORGANISM: Artificial Sequence
<220> FEATURE:

```
<223> OTHER INFORMATION: Designed peptide containing a terminal amide
      group

<400> SEQUENCE: 32

Thr Gly Thr Gly
1

<210> SEQ ID NO 33
<211> LENGTH: 6
<212> TYPE: PRT
<213> ORGANISM: Artificial Sequence
<220> FEATURE:
<223> OTHER INFORMATION: Designed peptide containing a terminal amide
      group

<400> SEQUENCE: 33

Leu Met Trp Trp Met Leu
1               5

<210> SEQ ID NO 34
<211> LENGTH: 12
<212> TYPE: PRT
<213> ORGANISM: Artificial Sequence
<220> FEATURE:
<223> OTHER INFORMATION: Designed peptide containing a terminal amide
      group

<400> SEQUENCE: 34

Arg Ala Val Thr Leu Tyr Leu Gly Ala Val Ala Ala
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Designed peptide containing a terminal amide
      group

<400> SEQUENCE: 35

Arg Leu Leu Thr Ala Lys Met Leu Met Trp Trp Met Leu Arg
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Designed peptide containing a terminal amide
      group

<400> SEQUENCE: 36

Arg Ile Arg Lys Lys Leu Arg Tyr Ile Gly Ser Arg
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Designed peptide containing a terminal amide
      group

<400> SEQUENCE: 37

Arg Lys Lys Lys Arg Lys Val Tyr Ile Gly Ser Arg
1               5                   10
```

-continued

```
<210> SEQ ID NO 38
<211> LENGTH: 13
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 38

Leu Lys Arg Lys Leu Gln Arg Val Val Tyr Trp Leu Leu
1               5                   10
```